(12) United States Patent
Rudolph et al.

(10) Patent No.: US 9,709,480 B2
(45) Date of Patent: Jul. 18, 2017

(54) WEATHERING TESTING USING RADIATION SOURCES WHICH ARE IDENTIFIABLE BY MEANS OF RFID CHIPS

(71) Applicant: ATLAS MATERIAL TESTING TECHNOLOGY GMBH, Linsengericht-Altenhasslau (DE)

(72) Inventors: Bernd Rudolph, Alzenau (DE); Peter March, Frankfurt am Main (DE)

(73) Assignee: ATLAS MATERIAL TESTING TECHNOLOGY GMBH, Linsengericht-Altenhasslau (DE)

( * ) Notice: Subject to any disclaimer, the term of this patent is extended or adjusted under 35 U.S.C. 154(b) by 461 days.

(21) Appl. No.: 14/476,922

(22) Filed: Sep. 4, 2014

(65) Prior Publication Data
US 2015/0068327 A1    Mar. 12, 2015

(30) Foreign Application Priority Data
Sep. 6, 2013  (EP) .................................. 13183391

(51) Int. Cl.
*G01N 17/00*    (2006.01)
(52) U.S. Cl.
CPC ......... *G01N 17/004* (2013.01); *G01N 17/002* (2013.01)
(58) Field of Classification Search
None
See application file for complete search history.

(56) References Cited

U.S. PATENT DOCUMENTS

| 4,831,564 | A | 5/1989 | Suga | |
|---|---|---|---|---|
| 5,136,886 | A | 8/1992 | Neigoff et al. | |
| 6,467,911 | B1* | 10/2002 | Ueyama | F21V 17/00 348/E5.137 |
| 2002/0139928 | A1 | 10/2002 | Rathod et al. | |
| 2004/0149922 | A1 | 8/2004 | Rathod et al. | |
| 2004/0231440 | A1* | 11/2004 | Beraud | G01N 33/442 73/865.6 |
| 2005/0121605 | A1 | 6/2005 | Rathod et al. | |
| 2005/0167580 | A1* | 8/2005 | Scott | G01N 17/002 250/252.1 |
| 2006/0285325 | A1* | 12/2006 | Ducharme | H05B 33/0857 362/231 |
| 2008/0156120 | A1* | 7/2008 | D'Ambrosio | G01N 17/004 73/865.6 |
| 2008/0185539 | A1 | 8/2008 | Mastenbroek et al. | |
| 2013/0169951 | A1* | 7/2013 | Miura | G01N 21/33 356/51 |

FOREIGN PATENT DOCUMENTS

| DE | 102006060418 | 6/2008 |
|---|---|---|
| EP | 2506687 | 10/2012 |

OTHER PUBLICATIONS

Extended European Search Report issued Oct. 16, 2013, in corresponding European Patent Application No. 13183391.5.

* cited by examiner

*Primary Examiner* — Robert R Raevis
(74) *Attorney, Agent, or Firm* — Staas & Halsey LLP

(57) ABSTRACT

The apparatus has a weathering chamber, in which at least one sample can be arranged, and at least one radiation source, which are arranged in the weathering chamber, wherein the radiation source is provided with a storage device, on which data relating to the radiation source are stored.

6 Claims, 2 Drawing Sheets

WEATHERING TESTING USING RADIATION SOURCES WHICH ARE IDENTIFIABLE BY MEANS OF RFID CHIPS

CROSS-REFERENCE TO RELATED APPLICATIONS

This application claims the foreign priority benefit of European Application No. 13183391.5, filed Sep. 6, 2013, in the European Patent Office, the disclosure of which is incorporated herein by reference.

BACKGROUND

1. Field

The present invention relates to an apparatus for artificially weathering or testing the lightfastness of samples and to a radiation source for an apparatus for artificially weathering or testing the lightfastness of samples.

2. Description of Related Art

In apparatuses for artificial weathering, an assessment of the weathering-induced aging response of a sample, in particular a flat material sample, is performed, wherein the sample is subjected to artificial weathering. For this purpose, such apparatuses generally have a weathering chamber, in which holding means for holding samples to be weathered and a radiation source for applying radiation, in particular UV radiation, to the samples are arranged.

In such apparatuses for artificially weathering or testing the lightfastness of material samples, the intention is usually to estimate the life of materials which are continuously subjected to natural weather conditions during use and are therefore impaired under climatic influences such as sunlight, solar heat, moisture or the like. In order to obtain good simulation of the natural weathering conditions, it is advantageous if the spectral energy distribution of the light generated in the apparatus at least corresponds to that of the natural solar radiation, for which reason xenon gas discharge lamps are used as radiation source in such devices. In addition, accelerated aging testing of the materials is achieved substantially by virtue of very intensified radiation, in comparison with natural conditions, of the samples, as a result of which the aging of the samples is accelerated. Therefore, after a comparatively short period of time, it is possible to draw a conclusion on the long-term aging response of a material sample.

A large proportion of the material samples investigated in artificial weathering devices consists of polymeric materials. In the case of such materials, the weathering-induced impairment is substantially caused by the UV component of solar radiation. The photochemical primary processes occurring in the process, i.e. the absorption of photons and the generation of excited states or free radicals, are independent of temperature. Conversely, the subsequent reaction steps with the polymers or additives can be temperature-dependent, with the result that the observed aging of the materials is likewise temperature-dependent.

In the previously known weathering test devices, usually a xenon gas discharge lamp is used as radiation source since it is known that said lamp can simulate the solar spectrum quite well. However, other radiation sources, such as, for example, metal halide lamps or fluorescent lamps, are also conceivable for use in weathering test devices.

An important criterion for the operation of a radiation source within a weathering test device is its spectral quality. It is highly important that the lamps used generate the required sunlight-like spectrum over their entire life. In addition, the life of the radiation source is also of high importance since the radiation source is constantly operated under high loading in order to enable very intensified irradiation of the samples. Therefore, a constantly high quality of the radiation sources for the operation is of high importance to the customer. In the present situation, however, it is possible to use radiation sources of different origin and therefore potentially different quality in weathering test devices, wherein a possibly low quality often only becomes noticeable during operation by a premature discrepancy between the radiation spectrum and the solar spectrum, a premature decrease in the radiated power or even total failure. Furthermore, it is not possible at present, when using a radiation source which may have already been used earlier, for a customer to establish the history of this radiation source, for example the operating hours already provided, and to take this into consideration for the further operation of the radiation source, if appropriate.

SUMMARY

It is therefore the object of the present invention to specify an apparatus for artificially weathering or testing the lightfastness of samples and a radiation source for such an apparatus, by means of which information relating to a radiation source used by a customer can be provided to this customer.

This object is achieved by the features of the independent patent claims. Advantageous developments and configurations are the subject matter of dependent claims.

An essential concept of the present invention consists in providing, for the customer, improved identifiability of radiation sources to be used in weathering devices. In accordance with the present prior art, these radiation sources are in principle indistinguishable from one another for a customer and the customer, when a radiation source is inserted into a weathering test device, has no information in respect of whether the radiation source is, for example, an original product of the manufacturer and/or whether the radiation source may have already been used earlier. This can be improved by virtue of the fact that the radiation source is connected to a suitable storage device, on which data relating to the origin and/or the history of the radiation source can be stored or storable.

An apparatus according to the invention for artificially weathering or testing the lightfastness of samples therefore has a weathering chamber, in which at least one sample can be arranged, and at least one radiation source, which is arranged in the weathering chamber, wherein each radiation source is provided with a storage device, in which data relating to the radiation source can be or are stored.

In accordance with one embodiment of the apparatus according to the invention, the data stored on the storage device can be used for the authorization and/or identification of the radiation source. It can be provided, for example, that, once a radiation source has been inserted into a weathering test device, firstly authorization takes place in such a way that it is checked whether this radiation source is an original product of a specific manufacturer. In particular, in the process a certain manufacturer-specific code stored on the storage device can be scanned. Provision can then furthermore be made for the user to be informed in a suitable manner of the result of the authorization test and for possibly the result of the test to be stored or logged in a control device of the weathering test device. Provision can also be made for the relevant radiation source to be enabled for operation only in the event of a positive result of the authorization test, but otherwise for operation of the radiation source to be automatically suppressed, for example by virtue of the supply of electric power to the radiation source being blocked. Otherwise, provision can also be made for the user to only be informed of the result of the authorization test, but furthermore for no restrictions to the operation of the radiation source to be made irrespective of the result of this test.

Provision can furthermore be made for the radiation source to be identified as a specific radiation source in order to make it distinguishable from other radiation sources, for example by means of an additional code, which is assigned uniquely to a specific radiation source. As an alternative or in addition to this code, specific data can be stored on the storage device, which data uniquely characterize the radiation source with respect to its history, for example its date of manufacture, its association with a specific charge, a number within the charge, or, for example, operating hours which have already previously been provided and possibly the radiated power which has been output in earlier operating hours and which can be measured by a sensor, and possibly a residual life of the radiation source resulting from this data.

In accordance with one embodiment of the apparatus according to the invention, the storage device is in the form of part of an electronic circuit, in particular an RFID chip or RFID tag. In respect of its supply of energy, the RFID chip can be configured so as to be passive or active, wherein, in the passive design, electric power is supplied to said RFID chip via the RF radiation transmitted to it and, in the active form, it has an internal energy supply source, such as a battery or a rechargeable battery.

In accordance with one embodiment of the apparatus according to the invention, the storage device is designed in such a way that data, such as, for example, the operating hours provided by the radiation source or a residual life calculated therefrom, can be stored on said storage device and in particular can be overwritten over the course of the further operating duration of the radiation source.

In accordance with one embodiment of the apparatus according to the invention, said apparatus has a control device, which is designed to store data on the storage device and to read data from the storage device. In particular for the case where the storage device is part of an RFID chip, the control device is coupled to an RFID read device or contains such an RFID read device.

In accordance with one embodiment of the apparatus according to the invention, the at least one radiation source is formed by a xenon gas discharge lamp. However, other radiation sources such as metal halide lamps or fluorescent lamps are also conceivable as radiation sources.

In accordance with one embodiment of the apparatus according to the invention, the storage device is to a certain extent connected nondetachably to the radiation source, which is intended to mean that the storage device cannot be detached from the radiation source by a customer without any damage being caused. This is intended to serve the purpose of preventing any attempts at tampering.

In accordance with one embodiment of the apparatus according to the invention, the radiation source can also be connected to a further element for authorizing and/or identifying the radiation source, for example a barcode, which can provide additional information on the radiation source.

In accordance with one embodiment of the apparatus according to the invention, said apparatus has a plurality of radiation sources, which are independently operable, wherein provision can be made for each radiation source to have a storage device in accordance with the invention.

In accordance with one embodiment of the apparatus according to the invention, said apparatus has a control device, which is configured to generate control signals for actuating the at least one radiation source and, in the case of a plurality of radiation sources, has a plurality of outputs, which are connectable to the plurality of radiation sources. In particular, provision can be made for the control device to be configured to determine an optimum operating mode in which the radiation sources are subjected to as little loading as possible on the basis of a combined radiated power of the radiation sources desired by a user. Provision can be made, for example, for the storage device of each of the radiation sources to be readable by the control device, and for the read value of the operating hours already previously provided by the radiation sources and/or of the residual life of the radiation sources determined therefrom to be used by the control device for determining the optimum operating mode. For the purpose of the determination of the optimum operating mode, an expert system can be contained in the control device, for example.

The present invention likewise relates to a radiation source for an apparatus for artificially weathering or testing the lightfastness of samples, which radiation source is provided with a storage device, in which data relating to the radiation source are stored or storable.

Further embodiments of the radiation source according to the invention can be formed in accordance with the above-described embodiments for the apparatus for artificial weathering or testing of lightfastness.

BRIEF DESCRIPTION OF DRAWINGS

The invention will be explained in greater detail below with reference to exemplary embodiments in conjunction with the figures in the drawing, in which.

DESCRIPTION OF EMBODIMENTS

Figure 1A:
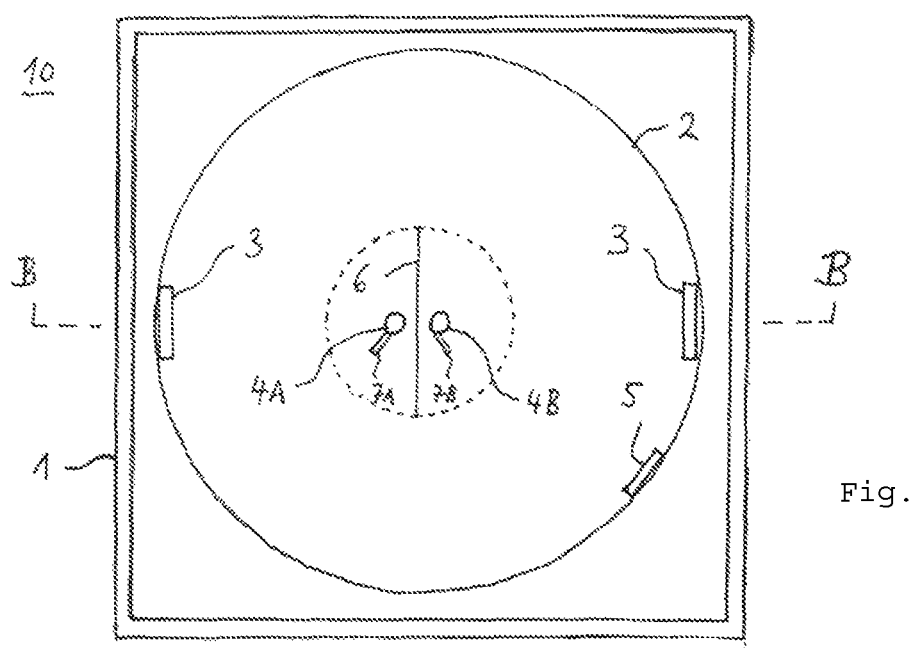
FIGS. 1A, B show a schematic illustration of an embodiment of an apparatus according to the invention for artificially weathering or testing the lightfastness of samples in a cross section (A) and a longitudinal section (B).
Figure 1B:
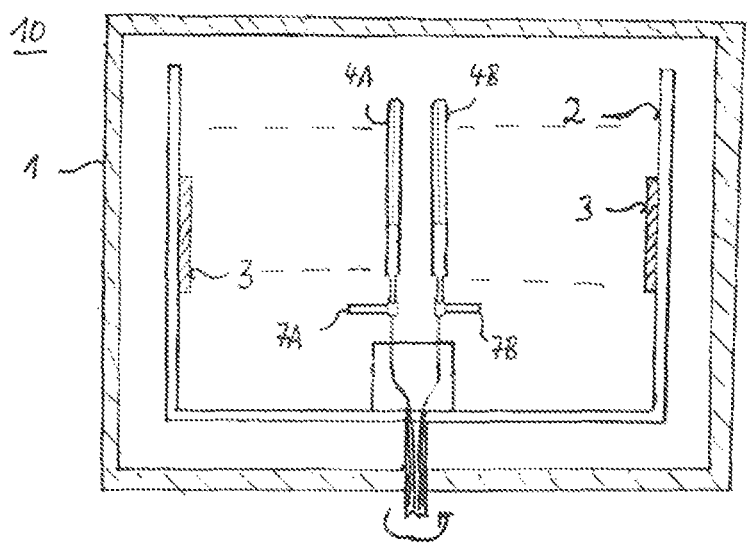

FIGS. 1A, B show an apparatus 10 according to the invention for artificially weathering or testing the lightfastness of samples in a cross section (A) and a longitudinal section (B), schematically. Each of the radiation sources 4A and 4B is connected to a storage device 7A and 7B, respectively, which can in particular have an RFID chip or another electronic storage device.

Figure 2:
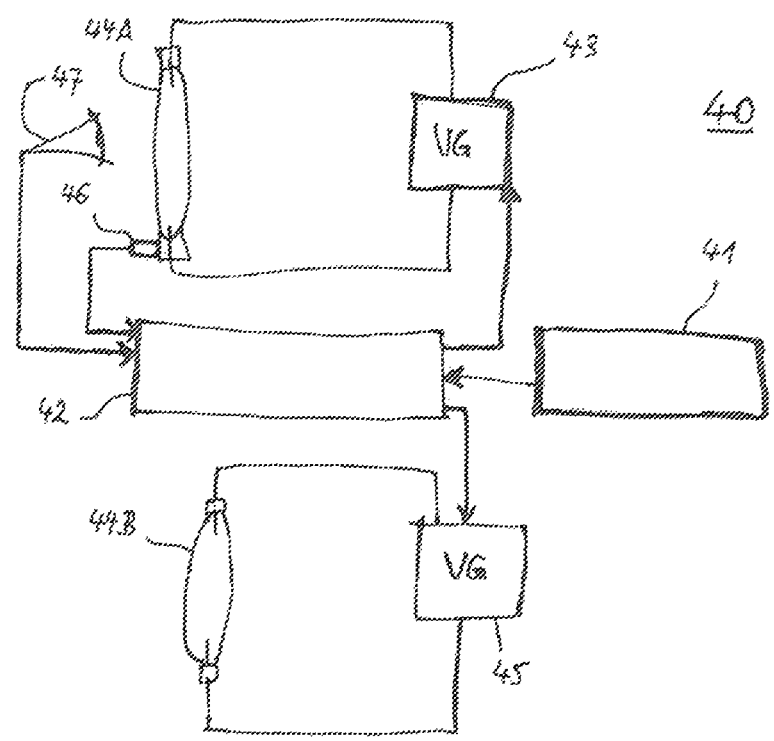
FIG. 2 shows a schematic block circuit diagram of a circuit for actuating two radiation sources of an apparatus for artificially weathering or testing the lightfastness of samples.

The apparatus 10 comprises a weathering chamber 1, within which artificial weathering or testing of the lightfastness of samples can be performed. An annularly closed holding frame 2 is mounted rotatably in the weathering chamber 1 and has, on its inner side, suitably shaped holding elements (not shown), by means of which samples 3 or workpieces, for example rectangular varnished samples of standardized size, can be held. The holding frame 2 is in particular circular in a lateral cross section, with the result that the samples 3 are guided on a closed circular path on rotation of the holding frame 2. Two radiation sources 4A and 4B are arranged within the holding frame 2 and substantially concentrically therewith and can be formed by, for example, xenon gas discharge lamps. It is also possible for more than two radiation sources to be provided. In particular, three radiation sources can be arranged in such a way that they come to lie, in cross section, at the corners of an equilateral triangle. As illustrated in FIG. 2, the two radiation sources 4A and 4B can be formed by elongate or longitudinal radiation bodies, in particular glass bulbs, which are aligned parallel to one another. The entire arrangement can be rotationally symmetrical such that an axis of rotation of the rotary movement of the holding frame 2 coincides with a mid-axis or axis of symmetry of the two radiation sources 4A and 4B. Provision may be made for it to be possible for a plurality of samples 3 to be fastened on the holding frame 2, in particular on holding elements provided for this purpose and arranged in the circumferential direction of the holding frame 2. Moreover, the samples 3 can also be fastened on the holding frame 2 one above the other in a plurality of places. The radiation sources 4A and 4B can be operable or actuable independently of one another, as will be mentioned in more detail further below.

Furthermore, a radiation sensor 5 can be arranged in the weathering chamber 1 and detects the radiated power of the radiation emitted by the radiation sources 4A and 4B. The radiation sensor 5 can be fastened, in the same way as the samples 3, on the holding frame 2 and revolve with said samples around the radiation arrangement comprising the two radiation sources 4A, B, i.e. can be in the form of a concurrent radiation sensor 5. The output signal of the radiation sensor 5 can be supplied to an external control device, as will be described in more detail below. The radiation sensor 5 can be designed in such a way that it outputs an instantaneous radiated power detected by said radiation sensor as a corresponding electrical measurement signal. Provision can furthermore be made for an absorber plate 6 to be arranged between the radiation sources 4A and 4B so that the radiation sensor 5 detects in each case only the radiation emitted by one of the radiation sources 4A, B in any conceivable position on its orbit. The radiation sensor 5 can, as illustrated, be arranged offset with respect to the samples 3 in the circumferential direction of the holding device 2. It could likewise readily be arranged offset with respect to the samples 3 in the vertical direction even without any circumferential offset or be arranged offset with respect to the samples 3 both in the vertical and circumferential directions.

The weathering chamber 1 can, in a manner known per se, have further devices for artificial weathering, such as, for example, moisture generators or the like, but no further details of these are provided below. It is also possible, for example, for an air flow to be introduced into the weathering chamber 1, which air flow sweeps past the samples 3 and/or the radiation sources 4A and 4B in the vertical direction.

Stationary radiation sensors can also be arranged in the weathering chamber 1 instead of the concurrent radiation sensor 5 or in addition thereto, which stationary radiation sensors detect the radiated power of the radiation emitted by the radiation sources 4A and 4B. The radiation sensors can be arranged fixedly within the weathering chamber 1 and they can in particular be arranged in such a way that each of the radiation sensors in each case only detects the radiated power emitted by one of the two radiation sources 4A and 4B. The output signals of the radiation sensor(s) can be supplied to an external control device, as will be described in more detail below.

FIG. 2 shows a block circuit diagram illustrating the actuation of the radiation sources of an apparatus for artificial weathering or testing of lightfastness. The circuit arrangement 40 serves the purpose of actuating two different radiation sources 44A and 44B independently of one another. The radiation sources in FIG. 2 can be formed by gas discharge lamps, in particular xenon gas discharge lamps, which can each be connected to ballasts. A first radiation source 44A can therefore be connected with its connection contacts to a first ballast 43, and a second radiation source 44B can be connected with its connection contacts to a second ballast 45.

The circuit arrangement 40 can furthermore have a user interface 41, by means of which a user can initiate a test run for testing of weathering or testing of lightfastness of samples by inputting a certain operating mode or certain desired parameters. The user interface 41 can be provided by a keyboard, in particular the keyboard of a PC. A desired parameter can be, for example, a radiated power to be emitted by each of the two radiation sources 44A and 44B or else a total radiated power to be achieved additively by both radiation sources. The user interface 41 can be connected on the output side to a control device 42, such as a microcontroller or microprocessor. The control device 42 can have two different outputs, which can be connected to the two ballasts 43 and 45. The control device 42 can therefore be capable of actuating the ballasts 43 and 45 and therefore ultimately the radiation sources 44A and 44B differently, in particular on the basis of an input by a user at the user interface 41. It is possible, for example, for a specific program mode with a specific, preset designation (for example XenoLogic) to be provided which is selectable by the user and which the control device 42 instructs to operate the radiation sources 44A and 44B taking into consideration a total radiated power additionally also input by the user in such a way that a maximum service life results for both radiation sources. This can mean, for example, that when a test run is started, only one of the two radiation sources is operated for a preset period of time and then the second radiation source is connected thereto. However, should a total radiated power of 60 W/cm2 be desired by a user, for example (depending on the lamp type and at a specific distance from the lamp), provision can also be made for both radiation sources to be operated at a radiated power of 30 W/cm2 from the beginning.

In addition to these presets, further information can also be supplied to the control device 42 by the user interface 41, which information can be used by said control device for controlling the radiation sources 44A and 44B. Thus, for example, as shown in the previous exemplary embodiments, a radiation sensor 47 can be provided which individually detects the radiation emitted by the radiation source 44A and transfers a measurement signal representing the detected radiated power to the control device 42. The radiation sensor 47 can be in the form of a revolving radiation sensor. In the illustration in FIG. 2, the radiation sensor 47 is instantaneously oriented to the radiation source 44A and therefore instantaneously measures the emitted radiated power thereof. If, for example, the performance of the radiation source 44A should now decline and the radiation sensor should detect this correspondingly and signal this to the control device 42, the control device 42 can provide for a correspondingly higher electric power to be provided to the ballast 43. In the same way, the radiation emitted by the second radiation source 44B can also be detected by the radiation sensor 47 (or a further radiation sensor) and a measurement signal representing the radiated power provided to the control device 42.

Provision can be made for one or both of the radiation sources 44A and 44B to be provided with a storage device 46, in particular an electronic circuit such as an RFID chip, on which, for example, as described further above, a manufacturer-specific code and/or further data, such as the operating hours provided by the radiation source, can be stored. The RFID chip 46 can be connected, in particular non-detachably, to the respective radiation source, and in particular provision can be made for it not to be possible for it to be disconnected from the radiation source by a user without any damage being caused. During operation of the radiation source, it is possible to measure, for example by means of a radiation sensor, how long and at what output radiated power the radiation source has already been operated and the result can be evaluated by the control device 42 and stored on the electronic circuit 46. Each time the radiation source is brought into operation again, first the electronic circuit 46 can be read and the result can be supplied to the control device 42, which takes into consideration this result for its calculation of the optimum operating mode of said radiation source and the other radiation sources for a subsequent test run. Furthermore, provision can also be made for an expert system to be stored in the control device 42, to which expert system all of the data, in particular sensor data, remaining life data, desired total radiated power, etc., can be supplied, and which thereupon decides the way in which the radiation sources should be operated with the aim of achieving as long a service life as possible.

Although specific embodiments have been illustrated and described in this description, a person skilled in the art will recognize that the specific embodiments shown and described can be replaced with a multiplicity of alternative and/or equivalent implementations without departing from the scope of protection of the present invention. This application is intended to disclose any modifications or changes to the specific embodiments set forth in this document. It is therefore provided that this invention is only limited by the claims and equivalents thereof.

What is claimed:
1. An apparatus for artificially weathering or testing the lightfastness of samples, comprising:
    a weathering chamber configured to have at least one sample arranged therein;
    at least one radiation source, which is provided with a radio-frequency identification (RFID) chip as a storage device, the RFID chip being configured to store data relating to the at least one radiation source; and
    a control device configured to control the at least one radiation source, the control device including an RFID read device or being coupled to an RFID read device, the RFID read device being configured to read out the RFID chip of the at least one radiation source.
2. The apparatus as claimed in claim 1, wherein
    the storage device stores information which characterizes the at least one radiation source as originating from a specific manufacturer.
3. The apparatus as claimed in claim 1, wherein
    the storage device stores information relating to operating hours provided and/or a residual life of the at least one radiation source, and
    the information can be overwritten in the storage device over the course of an operating duration of the at least one radiation source.
4. The apparatus as claimed in claim 1, wherein
    the at least one radiation source is formed by a xenon gas discharge lamp.
5. The apparatus as claimed in claim 1, wherein
    the at least one radiation source includes a plurality of radiation sources, and each of the radiation sources are independently operable.
6. The apparatus as claimed in claim 5, wherein
    the control device is configured to generate control signals for actuating the radiation sources and has a plurality of outputs, which are connectable to the plurality of radiation sources.

\* \* \* \* \*